United States Patent [19]

Klang et al.

[11] Patent Number: 5,354,909
[45] Date of Patent: Oct. 11, 1994

[54] PROCESSES FOR ISOLATING HYDROXYALDEHYDE ISOMERS

[75] Inventors: Jeffrey A. Klang, Exton, Pa.; Ann P. Lawson, Lancashire, Del.

[73] Assignee: ARCO Chemical Technology, L.P., Wilmington, Del.

[21] Appl. No.: 108,090

[22] Filed: Aug. 17, 1993

[51] Int. Cl.$^5$ ............................................. C07C 45/78
[52] U.S. Cl. .................................. 568/492; 568/438; 568/449
[58] Field of Search ..................... 568/492, 438, 449

[56] References Cited

U.S. PATENT DOCUMENTS

| | | | |
|---|---|---|---|
| 4,123,444 | 10/1978 | Smith | 260/347.8 |
| 4,139,542 | 2/1979 | Smith | 260/347.8 |
| 4,678,857 | 7/1987 | Dureanleau et al. | 568/492 |
| 5,252,188 | 10/1993 | Stradal et al. | 568/492 |
| 5,254,702 | 10/1993 | Lawson et al. | 549/475 |

FOREIGN PATENT DOCUMENTS

| | | | |
|---|---|---|---|
| 373443 | 6/1990 | European Pat. Off. | 568/492 |
| 52-106860 | 9/1977 | Japan . | |
| 3261775 | 11/1991 | Japan . | |

OTHER PUBLICATIONS

"Protective Groups In Organic Synthesis" (New York 1991) by Theodora W. Greene & Peter Wuts; published by John Wiley & Sons (pp. 36 & 37).

Primary Examiner—Werren B. Lone
Attorney, Agent, or Firm—Jonathan L. Schuchardt

[57] ABSTRACT

A process for isolating 4-hydroxybutanal and 3-hydroxy-2-methylpropanal from aqueous mixtures of the isomers is disclosed. Reaction of the aqueous mixture with a hydroxy compound in the presence of an acidic catalyst and a nonpolar organic solvent gives a product aqueous solution of 3-hydroxy-2-methylpropanal and an organic solution containing a 2-oxytetrahydrofuran derived from 4-hydroxybutanal. The 4-hydroxybutanal can be regenerated by acidic hydrolysis of the 2-oxytetrahydrofuran.

20 Claims, No Drawings

PROCESSES FOR ISOLATING HYDROXYALDEHYDE ISOMERS

FIELD OF THE INVENTION

The invention relates to processes for isolating hydroxyaldehyde isomers. In particular, aqueous mixtures of 4-hydroxybutanal and 3-hydroxy-2-methylpropanal are separated by selectively converting only 4-hydroxybutanal to a 2-oxytetrahydrofuran derivative.

BACKGROUND OF THE INVENTION

A commercially important route to 1,4-butanediol and 2-methyl-1,3-propanediol involves isomerization of propylene oxide to allyl alcohol, followed by hydroformylation of allyl alcohol using a rhodium catalyst to give a mixture of 4-hydroxybutanal and 3-hydroxy-2-methylpropanal. Catalytic hydrogenation of the aldehyde mixture gives mostly 1,4-butanediol and a minor proportion of 2-methyl-1,3-propanediol. The diols are useful chemical intermediates for making polyesters, polyurethanes, thermoplastic elastomers, and other useful products.

The aldehyde mixture from hydroformylation is usually separated from the rhodium catalyst solution by extraction into water. This aqueous stream is a relatively inexpensive source of both 4-hydroxybutanal and 3-hydroxy-2-methylpropanal. Each of these compounds is valuable in pure form as a chemical intermediate for making pure diols useful in polyesters, polyurethanes, and alkyd resins. Unfortunately, the similarity in boiling points and solubility characteristics of the aldehyde isomers complicates their separation and use as pure compounds.

Matsumoto teaches that 4-hydroxybutanal can be separated from aqueous media by vacuum distillation (see Japanese Patent Application Kokai No. 3-261775), but does not teach how to separate 4-hydroxybutanal from 3-hydroxy-2-methylpropanal.

In copending application Ser. No. 07/868,050, filed Apr. 13, 1992, now U.S. Pat. No. 5,254,702 we disclose a two-phase process for producing a 2-oxytetrahydrofuran by reacting an aqueous solution of 4-hydroxybutanal with a hydroxy compound in an organic solvent in the presence of an acid catalyst. The 2-oxytetrahydrofuran product is isolated from the organic phase by any suitable method. Isolation of individual aldehyde isomers from the aqueous aldehyde mixture is not taught.

A practical process for isolating 4-hydroxybutanal and 3-hydroxy-2-methylpropanal in pure form is needed. In particular, a process that overcomes the need to separate the isomers based on boiling point or solubility differences would be valuable. Preferably, the process would be effective to cleanly and efficiently isolate either or both aldehyde isomers.

SUMMARY OF THE INVENTION

In one aspect, the invention is a process for isolating 3-hydroxy-2-methylpropanal from an aqueous mixture of 4-hydroxybutanal and 3-hydroxy-2-methylpropanal. The aqueous aldehyde mixture is reacted in a two-phase mixture with a hydroxy compound in the presence of an acid catalyst and a nonpolar organic solvent. The resulting aqueous solution contains 3-hydroxy-2-methylpropanal, while the organic phase contains a 2-oxytetrahydrofuran product derived from 4-hydroxybutanal and the hydroxy compound. The aqueous and organic phases are separated, and the desired 3-hydroxy-2-methylpropanal is isolated from the aqueous solution by any suitable means, including extraction or distillation.

In another aspect, the invention is a process for isolating 4-hydroxybutanal from an aqueous mixture of 3-hydroxy-2-methylpropanal and 4-hydroxybutanal. The aqueous aldehyde mixture is reacted with a hydroxy compound as described above. Following separation of the aqueous and organic phases, the 2-oxytetrahydrofuran product is isolated from the organic solution, and is reacted with water in the presence of a second acid catalyst to generate an aqueous solution of 4-hydroxybutanal that is substantially free of 3-hydroxy-2-methylpropanal.

DETAILED DESCRIPTION OF THE INVENTION

In the processes of the invention, an aqueous mixture of 4-hydroxybutanal and 3-hydroxy-2-methylpropanal reacts with a hydroxy compound in the presence of an acid catalyst and a nonpolar organic solvent to produce a product aqueous solution that contains 3-hydroxy-2-methylpropanal and a product organic solution that contains a 2-oxytetrahydrofuran. The 2-oxytetrahydrofuran is the reaction product of 4-hydroxybutanal and the hydroxy compound.

The initial aqueous aldehyde mixture can contain any proportion of 4-hydroxybutanal and 3-hydroxy-2-methylpropanal. A preferred aqueous aldehyde solution is the one conveniently available from a commercial process involving hydroformylation of allyl alcohol. The aqueous stream from this process typically contains about 10–13 wt. % aldehydes, and this solution is suitable for use in the invention without modification. Typically, 4-hydroxybutanal is the major component in the mixture (although the process of the invention can be used for mixtures having mostly 3-hydroxy-2-methylpropanal). It is generally recognized that, in aqueous media, 4-hydroxybutanal equilibrates with 2-hydroxytetrahydrofuran. For the purposes of this application, these compounds are interchangeable, and the goal is to separate either of these from 3-hydroxy-2-methylpropanal.

A hydroxy compound reacts with the aldehyde mixture. The hydroxy compound is any organic compound that has a free primary, secondary, or tertiary hydroxyl group. Suitable hydroxy compounds include saturated and unsaturated linear, branched, and cyclic aliphatic and aromatic alcohols. Diols, triols, and polyols are suitable. Polyether and polyester polyols such as polypropylene glycols, polytetramethylene ether glycols, and the like are suitable. Glycol ethers such as propylene glycol methyl ether and dipropylene glycol ethyl ether are also suitable. Preferred hydroxy compounds are aliphatic alcohols having from 1 to 10 carbons. The hydroxy compound preferably has good solubility in the nonpolar organic solvent used, although this is not required.

The amount of hydroxy compound used is generally not critical. However, the preferred amount for use varies, and depends on whether the goal is to isolate 4-hydroxybutanal, 3-hydroxy-2-methylpropanal, or both aldehydes. The preferred amount also depends on the relative ratio of aldehydes in the mixture. When the goal is to isolate pure 3-hydroxy-2-methylpropanal, it is preferred to use an amount of hydroxy compound sufficient to convert substantially all of the 4-hydroxybutanal present in the aqueous mixture to the 2-oxytetrahydrofuran. Thus, it is preferred to use at least about 1 equivalent of hydroxy compound per equivalent of 4-hydroxybutanal when the goal is to isolate pure 3-hydroxy-2-methylpropanal. A large excess (5 or more equivalents) of the hydroxy compound can be used if desired.

When the goal is to isolate 4-hydroxybutanal, the amount of hydroxy compound used is also most preferably the amount needed to convert substantially all of the 4-hydroxybutanal present in the aqueous mixture to the 2-oxytetrahydrofuran. However, a substantially pure 4-hydroxybutanal product can be isolated from the process of the invention by converting less than all of the 4-hydroxybutanal initially present to a 2-oxytetrahydrofuran product. Any 2-oxytetrahydrofuran product formed is extracted preferentially into the organic phase, and is cleanly separated from the water-soluble 3-hydroxy-2-methylpropanal. Thus, when a pure 2-oxytetrahydrofuran product (pure 4-hydroxybutanal precursor) is desired, the amount of hydroxy compound is preferably at least about 0.1 equivalents per equivalent of 4-hydroxybutanal, and is most preferably at least about 1 equivalent per equivalent of 4-hydroxybutanal.

An acid catalyst is used in the processes of the invention, both for converting 4-hydroxybutanal to a 2-oxytetrahydrofuran (referred to below as "the acid catalyst" or the "first acid catalyst"), and for regenerating 4-hydroxybutanal from the 2-oxytetrahydrofuran (referred to below as "the acid catalyst" or "the second acid catalyst"). The same acid can be used in both processes, or different acid catalysts can be selected.

The acid can be an organic acid such as acetic acid, trifluoroacetic acid, methanesulfonic acid, p-toluenesulfonic acid, or the like. Soluble inorganic acids such as hydrochloric acid and sulfuric acid are also suitable. Insoluble acids such as acidic ion-exchange resins, acid-washed clays, zeolites, and the like can be used. Preferred acid catalysts, because they are easily separated from the other components and reused, are the insoluble acids.

Any desired amount of acid catalyst can be used. As is well understood by those skilled in the art, the amount of catalyst needed will depend on many factors, including the specific reaction conditions used and the type of acid catalyst employed. With organic acids and soluble inorganic acids, a trace amount of catalyst usually suffices. Larger amounts of insoluble acids are typically used.

A nonpolar organic solvent is used in the processes of the invention. The nonpolar organic solvent is substantially water-immiscible. Combination of the nonpolar organic solvent with the aqueous mixture of 4-hydroxybutanal and 3-hydroxy-2-methylpropanal results in a two-phase mixture. Suitable nonpolar organic solvents are those in which the 2-oxytetrahydrofuran product is soluble. Suitable solvents include aliphatic and aromatic hydrocarbons, halogenated hydrocarbons, ketones, esters, ethers, and the like, and mixtures thereof. Preferred solvents are aliphatic and aromatic hydrocarbons. Hexane is particularly preferred. Preferred nonpolar organic solvents are those that can be readily separated from the 2-oxytetrahydrofuran product by distillation.

Reaction of the two-phase mixture results in a product aqueous solution that contains 3-hydroxy-2-methylpropanal and a product organic solution that contains a 2-oxytetrahydrofuran product derived from 4-hydroxybutanal and the hydroxy compound. Preferably, the reaction is performed in a continuous extraction unit. The product aqueous and organic solutions are separated. In one process of the invention, 3-hydroxy-2-methylpropanal, which is substantially purified of 4-hydroxybutanal, is then isolated from the product aqueous solution by any convenient means, preferably by extraction or distillation.

In another process of the invention, the primary object is to isolate substantially pure 4-hydroxybutanal. In this process, following separation of the product aqueous and organic solutions, the 2-oxytetrahydrofuran is isolated from the product organic solution by any convenient means, preferably by distillation. The 2-oxytetrahydrofuran is then reacted with an excess amount of water in the presence of a second acid catalyst to generate an aqueous solution of 4-hydroxybutanal that is substantially free of 3-hydroxy-2-methylpropanal. The 4-hydroxybutanal is then isolated from the aqueous solution by any convenient means, preferably by extraction or distillation. Additional methods of acid hydrolysis suitable for converting the 2-oxytetrahydrofuran to 4-hydroxybutanal are known in the art. Some of these are described in Greene et al., *Protective Groups in Organic Synthesis,* 2nd ed. (1981), p. 36.

If desired, the processes of the invention can be combined to isolate both hydroxyaldehyde isomers in substantially pure form. The product aqueous phase is purified to recover substantially pure 3-hydroxy-2-methylpropanal, while the product organic phase containing the 2-oxytetrahydrofuran is subjected to acidic hydrolysis to generate 4-hydroxybutanal.

Another way to practice the invention is to react the two-phase mixture as described above, separate the product aqueous and organic solutions, and then react the product organic solution with water in the presence of the second acid catalyst. In this process, the 2-oxytetrahydrofuran is not isolated from the product organic solution before acidic hydrolysis. The 4-hydroxybutanal generated by acidic hydrolysis is extracted preferentially into the aqueous phase. Preferably, the aqueous solution containing 4-hydroxybutanal is separated from the extracted organic phase, and 4-hydroxybutanal is isolated by any convenient means, preferably extraction or distillation.

The processes of the invention can be performed batchwise, semi-batchwise, or continuously, as desired. A continuous process is preferred.

Reaction of the two-phase mixture to make the 2-oxytetrahydrofuran proceeds smoothly over a broad temperature range, and is most conveniently performed at temperatures within the range of about 20° C. to about 100° C. A more preferred range is from about 20° C. to about 40° C. The reaction is usually complete within 24 hours at room temperature, and will often be complete in less than an hour.

The acidic hydrolysis step is performed with an excess of water. Preferably, the weight ratio of water to 2-oxytetrahydrofuran used is at least about 5:1. The acidic hydrolysis step is most conveniently performed at temperatures within the range of about 0° C. to about 50° C. A more preferred range is from about 0° C. to about 20° C. The acidic hydrolysis is typically complete within about 1 h, and often within minutes of combining the acid and 2-oxytetrahydrofuran.

The following examples merely illustrate the invention. Those skilled in the art will recognize many variations that are within the spirit of the invention and scope of the claims.

EXAMPLE 1

Preparation of 2-Ethoxytetrahydrofuran

A liquid-liquid continuous extractor is charged with 47.3 g of an aqueous solution containing 4-hydroxybutanal (12.4 wt. %) and 3-hydroxy-2-methylpropanal (0.6 wt. %). Ethanol (6.4 g), concentrated sulfuric acid (1 mL), and enough hexane to fill the extractor (approximately 200 mL) are added to the extractor. The aqueous layer is continuously extracted with hexane for 4 h, and the layers are separated. The aqueous and organic phases are analyzed by gas chromatography (GC). The aqueous phase contains 2-ethoxytetrahydrofuran (0.2 wt. %), 4-hydroxybutanal (0.5 wt. %), and 3-hydroxy-2-methylpropanal (0.6 wt. %). The hexane phase contains 2-ethoxytetrahydrofuran, but no detectable amount of 4-hydroxybutanal or 3-hydroxy-2-methylpropanal. Evaporation of the hexane phase gives substantially pure 2-ethoxytetrahydrofuran (7.3 g).

EXAMPLES 2–5

Acidic Hydrolysis of 2-Ethoxytetrahydrofuran

Example 2

2-Ethoxytetrahydrofuran (1 g, prepared as in Example 1) is added in one portion to a mixture of water (10 g) and concentrated hydrochloric acid (1 mL). The mixture is stirred at room temperature for about 1 h. GC analysis reveals: ethanol (3.4 wt. %), 4-hydroxybutanal (4.8 wt. %), 2-ethoxytetrahydrofuran (0.9 wt. %), 4-(2-tetrahydrofuranyloxy)butanol (FOBA) (0.9 wt. %), and 2,2-oxybistetrahydrofuran (Bis-THF ether) (0.5 wt. %).

Example 3

2-Ethoxytetrahydrofuran (15.4 g) is added in one portion to a mixture of water (100 g) and concentrated hydrochloric acid (10 g) cooled to 0° C. The mixture is stirred at 0° C. for 15 min. GC analysis reveals: ethanol (4.3 wt. %), 4-hydroxybutanal (7.8 wt. %), 2-ethoxytetrahydrofuran (1.4 wt. %), FOBA (0.3 wt. %). Analysis after 1 h shows no change.

Example 4

2-Ethoxytetrahydrofuran (15.4 g) is added in one portion to a mixture of water (100 g) and AMBERLYST 15 resin (10 g, product of Rohm and Haas Company) cooled to 0° C. The mixture is stirred at 0° C. for 15 min. GC analysis reveals: ethanol (4.6 wt. %), 4-hydroxybutanal (8.0 wt. %), 2-ethoxytetrahydrofuran (2.0 wt. %), FOBA (0.3 wt. %). The mixture is allowed to stir for another hour. GC analysis shows: ethanol (4.9 wt. %), 4-hydroxybutanal (8.4 wt. %), 2-ethoxytetrahydrofuran (1.7 wt. %), FOBA (0.3 wt. %).

Example 5

2-Ethoxytetrahydrofuran (63 g) is added in one portion to a mixture of water (200 g) and AMBERLYST 15 resin (10 g) cooled to 0° C. The mixture is stirred at 0° C. for 1 h. GC analysis reveals: ethanol (6.9 wt. %), 4-hydroxybutanal (12.9 wt. %), 2-ethoxytetrahydrofuran (3.8 wt. %), FOBA (1.0 wt. %). The AMBERLYST resin is filtered from mixture, and the filtrate is heated to 40° C. at 10 mm Hg. GC analysis shows: 4-hydroxybutanal (21.0 wt. %), ethanol (0.2 wt. %), 2-ethoxytetrahydrofuran (0.2 wt. %), FOBA (2.1 wt. %).

The preceding examples are meant as illustrations. The invention is defined by the following claims.

We claim:

1. A process for isolating 3-hydroxy-2-methylpropanal from a mixture of 3-hydroxy-2-methylpropanal and 4-hydroxybutanal, said process comprising:
   (a) reacting a two-phase mixture of:
      (i) an aqueous solution containing 3-hydroxy-2-methylpropanal and 4-hydroxybutanal; and
      (ii) a hydroxy compound; in the presence of an acid catalyst selected from the group consisting of soluble inorganic acids, organic acids, and insoluble acids, and a nonpolar organic solvent to produce a product aqueous solution that contains 3-hydroxy-2-methylpropanal and a product organic solution that contains a 2-oxytetrahydrofuran derived from 4-hydroxybutanal and the hydroxy compound;
   (b) separating the product aqueous solution from the product organic solution; and
   (c) isolating 3-hydroxy-2-methylpropanal from the product aqueous solution.

2. The process of claim 1 wherein steps (a) and (b) of the process are performed by continuous extraction.

3. The process of claim 1 wherein 3-hydroxy-2-methylpropanal is isolated from the product aqueous solution in step (c) by extraction.

4. The process of claim 1 wherein 3-hydroxy-2-methylpropanal is isolated from the product aqueous solution in step (c) by distillation.

5. The process of claim 1 wherein the hydroxy compound is selected from the group consisting of saturated and unsaturated linear, branched, and cyclic aliphatic and aromatic alcohols, including diols, triols, and polyols.

6. The process of claim 1 wherein the nonpolar organic solvent is selected from the group consisting of aliphatic and aromatic hydrocarbons.

7. The process of claim 1 wherein the acid catalyst is an insoluble acid catalyst.

8. A process for isolating 4-hydroxybutanal from a mixture of 4-hydroxybutanal and 3-hydroxy-2-methylpropanal, said process comprising:
   (a) reacting a two-phase mixture of:
      (i) an aqueous solution containing 4-hydroxybutanal and 3-hydroxy-2-methylpropanal; and
      (ii) a hydroxy compound; in the presence of a first acid catalyst selected from the group consisting of soluble inorganic acids, organic acids, and insoluble acids, and a nonpolar organic solvent to produce a product aqueous solution that contains 3-hydroxy-2-methylpropanal and a product organic solution that contains a 2-oxytetrahydrofuran derived from 4-hydroxybutanal and the hydroxy compound;
   (b) separating the product aqueous solution from the product organic solution;
   (c) isolating the 2-oxytetrahydrofuran from the product organic solution; and
   (d) reacting the 2-oxytetrahydrofuran with water in the presence of a second acid catalyst selected from the group consisting of soluble inorganic acids, organic acids, and insoluble acids, to generate an aqueous solution of 4-hydroxybutanal that is substantially free of 3-hydroxy-2-methylpropanal.

9. The process of claim 8 wherein steps (a) and (b) of the process are performed by continuous extraction.

10. The process of claim 8 wherein the 2-oxytetrahydrofuran is isolated from the product organic solution in step (c) by distillation.

11. The process of claim 8 wherein 4-hydroxybutanal is isolated from the aqueous solution generated in step (d) by extraction.

12. The process of claim 8 wherein 4-hydroxybutanal is isolated from the aqueous solution generated in step (d) by distillation.

13. The process of claim 8 wherein 3-hydroxy-2-methylpropanal is isolated from the product aqueous solution obtained in step (b).

14. The process of claim 8 wherein the hydroxy compound is selected from the group consisting of saturated and unsaturated linear, branched, and cyclic aliphatic and aromatic alcohols, including diols, triols, and polyols.

15. The process of claim 8 wherein the nonpolar organic solvent is selected from the group consisting of aliphatic and aromatic hydrocarbons.

16. The process of claim 8 wherein the first acid catalyst is an insoluble acid catalyst.

17. The process of claim 8 wherein the second acid catalyst is an insoluble acid catalyst.

18. A process for isolating 4-hydroxybutanal from a mixture of 4-hydroxybutanal and 3-hydroxy-2-methylpropanal, said process comprising:

(a) reacting a two-phase mixture of:
  (i) an aqueous solution containing 4-hydroxybutanal and 3-hydroxy-2-methylpropanal; and
  (ii) a hydroxy compound; in the presence of a first acid catalyst selected from the group consisting of soluble inorganic acids, organic acids, and insoluble acids, and a nonpolar organic solvent to produce a product aqueous solution that contains 3-hydroxy-2-methylpropanal and a product organic solution that contains a 2-oxytetrahydrofuran derived from 4-hydroxybutanal and the hydroxy compound;

(b) separating the product aqueous solution from the product organic solution;

(c) reacting the product organic solution with water in the presence of a second acid catalyst selected from the group consisting of soluble inorganic acids, organic acids, and insoluble acids, to generate (i) an aqueous solution of 4-hydroxybutanal that is substantially free of 3-hydroxy-2-methylpropanal, and (ii) an extracted organic phase.

19. The process of claim 18 wherein the aqueous solution of 4-hydroxybutanal produced in step (c) is separated from the extracted organic phase.

20. The process of claim 19 wherein the 4-hydroxybutanal is isolated from the aqueous solution in step (c) by distillation or extraction.

* * * * *